(12) United States Patent
Müller et al.

(10) Patent No.: US 6,867,326 B1
(45) Date of Patent: Mar. 15, 2005

(54) METHOD OF PRODUCING GLYPHOSATE OR A SALT THEREOF

(75) Inventors: Ulrich Müller, Neustadt (DE); Hans Rupert Merkle, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/031,234

(22) PCT Filed: Jul. 21, 2000

(86) PCT No.: PCT/EP00/07003

§ 371 (c)(1),
(2), (4) Date: Jan. 17, 2002

(87) PCT Pub. No.: WO01/07447

PCT Pub. Date: Feb. 1, 2001

(30) Foreign Application Priority Data

Jul. 23, 1999 (DE) ......... 199 34 599

(51) Int. Cl.$^7$ ............... C07F 9/22
(52) U.S. Cl. ............ 562/11; 562/16; 562/17
(58) Field of Search ............ 562/11, 16, 17

(56) References Cited

U.S. PATENT DOCUMENTS

| | | | |
|---|---|---|---|
| 3,950,402 A | 4/1976 | Franz | 260/502 |
| 3,954,848 A | 5/1976 | Franz | 260/502 |
| 3,969,398 A | 7/1976 | Hershman | 260/502 |
| 4,147,719 A | 4/1979 | Franz | 260/501 |
| 4,582,650 A | 4/1986 | Felthouse | 260/502 |
| 4,624,937 A | 11/1986 | Chou | 502/180 |
| 4,696,772 A | 9/1987 | Chou | 260/502 |
| 4,853,159 A | 8/1989 | Riley et al. | 562/17 |
| 4,965,402 A | 10/1990 | Riley et al. | 562/17 |
| 5,023,369 A | 6/1991 | Fields, Jr. | 562/17 |
| 5,091,561 A | 2/1992 | Riley et al. | 562/17 |
| 5,095,140 A * | 3/1992 | Fields, Jr. | 562/17 |
| 5,179,228 A * | 1/1993 | Martin Ramon et al. | 562/17 |
| 5,948,938 A * | 9/1999 | Nakano et al. | 562/17 |
| 5,962,729 A * | 10/1999 | Hayden et al. | 562/17 |

FOREIGN PATENT DOCUMENTS

| | | |
|---|---|---|
| EP | 0 019 445 | 11/1980 |
| EP | 0 162 035 | 11/1985 |
| EP | 0 314 662 | 5/1989 |
| EP | 0 464 017 | 1/1992 |
| EP | 0 464 018 | 1/1992 |
| EP | 0 472 693 | 3/1992 |
| ES | 2050624 | 5/1994 |
| WO | WO 96/19485 | 6/1996 |
| WO | WO 96/27602 | 9/1996 |
| WO | WO 96/38455 | 12/1996 |

* cited by examiner

*Primary Examiner*—Johann Richter
*Assistant Examiner*—Sikarl A. Witherspoon
(74) *Attorney, Agent, or Firm*—Keil & Weinkauf

(57) ABSTRACT

In a process for preparing N-phosphonomethylglycine or a salt thereof by bringing phosphonomethyliminodiacetic acid or a salt thereof into contact with at least one oxygen-containing oxidant in the presence of a heterogeneous catalyst, the heterogeneous catalyst comprises at least one silicate.

22 Claims, No Drawings

METHOD OF PRODUCING GLYPHOSATE OR A SALT THEREOF

The present invention relates to a novel process for preparing N-phosphonomethylglycine (glyphosate) or a salt thereof by bringing phosphonomethyliminodiacetic acid (PMIDE) into contact with at least one oxygen-containing oxidant in the presence of a heterogeneous catalyst comprising silicates.

Processes for preparing glyphosate and its salts are known per se. In all these, PMIDE or a salt thereof is reacted with an oxidant, e.g. a hydroperoxide- or an oxygen-containing gas, in the presence or absence of a catalyst to form glyphosate or a salt thereof. Thus, U.S. Pat. No. 3,954,848 describes the abovementioned reaction in the absence of a catalyst using oxidants defined therein at from about 70 to 100° C.

The reaction in the presence of gases comprising free oxygen using platinum, palladium, rhodium, iridium, ruthenium or osmium as metallic catalyst is described in U.S. Pat. No. 3,950,402.

U.S. Pat. No. 3,969,398 describes such a reaction in the presence of activated carbon. U.S. Pat. No. 4,582,650 describes a process for preparing N-phosphonomethylglycine by oxidative cleavage of N-phosphonomethyliminodiacetic acid with simultaneous oxidation of the formaldehyde formed as by-product in the presence of a catalyst system which comprises activated carbon together with a microporous acid-resistant aluminosilicate having a ratio of Si to Al of at least 2 as support and a noble metal as active component. According to this document, the process is carried out so that, or the catalyst is prepared so that, the noble metal is located in the pores of the support material and can thus not be poisoned by N-phosphonomethylamines.

The preparation of salts of glyphosate in the presence of platinum on activated carbon using an oxygen-containing gas is described in U.S. Pat. No. 4,147,719.

The Hungarian patent application HU 187 347 describes such a reaction using peroxides in the presence of a catalytic amount of silver, iron, tin, lead, manganese or molybdenum.

Such a reaction in aqueous suspension is described in EP-A 0 019 445. A process of the type in question using molecular oxygen in the presence of a catalyst selected from among salts and complex salts of manganese, cobalt, iron, nickel, bromine, ruthenium, aluminum, molybdenum, palladium and/or cerium at temperatures in the range from about 25 to 150° C. at atmospheric or subatmospheric pressure is described in EP-B 0 314 662 and the corresponding parallel patents.

A process for the selective preparation of secondary amines from tertiary amines, or of primary amines from secondary amines, by means of oxygen or an oxygen-containing gas in the presence of an activated carbon catalyst whose surface is free of oxides is described in EP-B 0 162 035 and its parallel patents. EP-A 0 464 017 and its parallel patents relate to a process for preparing glyphosate by oxidation of PMIDE by means of a peroxide in the presence of a catalytic amount of iron, zinc, aluminum, palladium or copper or water-soluble V, Fe or Cu compounds.

The use of water-soluble tungsten compounds or a mixture of a water-soluble tungsten compound and a water-soluble molybdenum compound in a process of the type in question is described in EP-A 0 464 018.

A process for preparing glyphosate by oxidation of PMIDE under superatmospheric pressure using oxygen or an oxygen-containing gas in the presence of a catalyst comprising noble metal on activated carbon as support is described in EP-B 0 472 693. In this process, the concentration of the noble metal in the reaction medium is reduced to less than 1 ppm.

A process of the type in question using hydrogen peroxide or oxygen-enriched air at pressures of from 100 to 1000 bar is described in WO 96/19485.

The conversion of PMIDE into glyphosate in the presence of $H_2O_2$ and activated carbon is described in WO 96/27602 and in WO 96/38455.

It is an object of the present invention to provide a novel process for preparing glyphosate by oxidative treatment of PMIDE, which process gives the target compound glyphosate in high yield.

We have found that this object is achieved by a process for preparing N-phosphonomethylglycine or a salt thereof by bringing phosphonomethyliminodiacetic acid or a salt thereof into contact with at least one oxygen-containing oxidant in the presence of a heterogeneous catalyst comprising at least one silicate.

As indicated above, PMIDE, which can be prepared by methods known from the prior art, is converted into glyphosate in the present process. In addition, salts of PMIDE can be converted into the corresponding glyphosate salts. Suitable salt-forming cations include alkali metals, alkaline earth metals, trimethylsulfonium, guanidinium, urea, ammonium and organic ammonium salts, e.g. the isopropylammonium salt. The latter can be obtained, for example, from organic amines, e.g. alkylamines, alkeneamines and alkanolamines, having not more than two amine groups. Suitable glyphosate salts are described, for example, in U.S. Pat. No. 4,147,719 and WO 96/38455, whose relevant contents are wholly incorporated by reference into the present application. These glyphosate salts are obtained as described below starting from the corresponding PMIDE salts, where the PMIDE salts used as starting materials can likewise be obtained by any methods known from the prior art, e.g. the reaction of PMIDE with, for example, NaOH. According to the present invention, both the monosalts and also the disalts of PMIDE can be used as starting materials and are in turn converted into the corresponding monoglyphosate or diglyphosate salts.

As oxidant in the process of the present invention, it is in principle possible to use any oxygen-containing oxidant. Particular mention may be made of organic peroxides, hydrogen peroxide, oxygen, oxygen-donating compounds and nitrogen oxides, e.g. $N_2O$. Organic peroxides include, for example, tert-butyl hydroperoxide, cumene hydroperoxide, peracetic acid, perbenzoic acid, peroxytrifluoroacetic acid, m-chloroperbenzoic acid, benzoyl peroxide, benzenepersulfonic acid. Apart from pure oxygen, all oxygen-containing gases such as air or mixtures of oxygen and inert diluent gases, e.g. helium, argon or nitrogen, can also be used. As oxygen-donating compounds, preference is given to the following: $H_2O_2$ and $H_2O_2$ prepared in-situ from $O_2$ and $H_2$. In particular, an aqueous $H_2O_2$ solution is used; this solution preferably has an $H_2O_2$ content of from 5 to 60% by weight.

The heterogeneous catalyst used according to the present invention comprises at least one silicate. Here too, it is possible to use all conceivable silicates. In particular, sheet silicates, naturally occurring or synthetically produced clay minerals, zeolites, clathrasils or mixtures of two or more thereof are used as silicates.

Zeolites are, as is known, crystalline aluminosilicates having ordered channel and cage structures and having pore openings in the micropore range below 0.9 nm. The network of such zeolites is built up of $SiO_4$ and $AlO_4$ tetrahedra which are joined via common oxygen bridges. An overview of the known structures may be found, for example, in M. W. Meier, D. H. Olson, Ch. Baerlocher "Atlas of Zeolite Structure Types", 4th edition, Elsevier, London, 1996.

To balance the negative charge resulting from incorporation of Al(III) into the Si(IV) silicate lattice, exchangeable cations are present in zeolites; in particular, these can be sodium, potassium, lithium or cesium cations, depending on the method of preparation. If these cations are replaced by protons, for example by ion exchange, the corresponding acidic solid having a zeolite structure in the H form is obtained.

Zeolites which contain no aluminum and in whose silicate lattice the Si(IV) is partly replaced by titanium as Ti(IV) are also known. These titanium zeolites, in particular those having a crystal structure of the MFI type, and possible ways of preparing them are described, for example, in EP-A 0 311 983 or EP-A 405 978. Apart from silicon and titanium, such materials can further comprise additional elements such as aluminum, zirconium, tin, iron, cobalt, nickel, gallium, boron or a small amount of fluorine. In the zeolite catalysts used in the process of the present invention, the titanium of the zeolite can be partly or wholly replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

It is known that titanium zeolites having an MFI structure can be identified by a particular X-ray diffraction pattern and also by means of a lattice vibration band in the infrared (IR) region at about 960 $cm^{-1}$.

Preference is given to using Ti, Ge, Te, V, Cr, Nb, Zr zeolites, in particular Ti zeolites.

Specific mention may be made of titanium-, vanadium-, chromium-, niobium- and zirconium-containing zeolites having a pentasil zeolite structure, in particular the types assigned X-ray crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MCM-22, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG, ZON and ITQ-4 structures and to mixed structures of two or more of the above-mentioned structures. Furthermore, the use of titanium-containing zeolites having the UTD-1, CIT-1 or CIT-5 structure in the process of the present invention is also conceivable. Further titanium-containing zeolites which may be mentioned are those having the ZSM-48 or ZSM-12 structure.

As particularly preferred catalysts, specific mention may be made of the titanium-containing zeolite catalysts generally referred to as "TS-1", "TS-2", "TS-3", "ZSM-48" and "ZSM-12", in each case with Ti, TTM-1, Ti-RUT, titanium-containing zeolites of the types "UTD-1", "CIT-5" and "SSZ-24", and also Ti zeolites having a structure isomorphous with β-zeolite.

For example, use is made of titanium zeolites as are known, for example from U.S. Pat. No. 3,329,481. In such titanium zeolites, part of the Si(IV) originally present in the silicate lattice is replaced by titanium as Ti(IV). Further titanium zeolites, in particular ones having a crystal structure of the MFI type, and possible ways of preparing them are described, inter alia, in U.S. Pat. No. 4,410,501, EP-A 0 311 983, U.S. Pat. No. 4,666,692, DE-A 3 047 798 or BE 1 001 038, whose relevant contents are wholly incorporated by reference into the present application. Further titanium-containing zeolites which can readily be used for the purposes of the present invention and have a structure different from the MFI structure are described, for example, in EP-A 0 405 978. Apart from silicon and titanium, such zeolites may further comprise additional elements such as aluminum (described, for example, in DE-A 31 41 283), gallium (EP-A 0 266 825), boron (U.S. Pat. No. 4,666,692) or small amounts of fluorine (EP-A 0 292 363). The content of the above-described publications relating to the zeolites described there is also wholly incorporated by reference into the present application.

Further zeolite catalysts which can be used in the process of the present invention are described, for example, in U.S. Pat. No. 5,430,000 and WO 94/29408, whose relevant contents are incorporated by reference into the present application.

Further titanium-containing zeolites which may be mentioned are those having a structure of ZSM-48 type, the ZSM-12 type, ferrierite or β-zeolite and of mordenite.

In addition, the following zeolite catalysts can be used in the process of the present invention:

Catalysts having a zeolite structure as are described in DE-A 196 23 611.8, whose contents relating to the catalysts described therein are hereby wholly incorporated by reference into the present application.

These are oxidation catalysts based on titanium silicates or vanadium silicates having a zeolite structure; as regards the zeolite structure, reference may be made to the structures indicated above as preferred. These catalysts are shaped by means of consolidating shaping processes as described in detail in the above-mentioned application.

In addition, the process of the present invention can be carried out using catalysts comprising at least one element selected from among the elements of groups Ia, IIa, IIIa, IVa, Va, VIa, VIIa, VIIIa, Ib, IIb, IIIb, IVb, Vb, VIb, VIIb of the Periodic Table.

It is also possible to use oxidation catalysts based on titanium silicates or vanadium silicates having a zeolite structure and a content of from 0.01 to 30% by weight of one or more noble metals selected from the group consisting of ruthenium, rhodium, palladium, osmium, iridium, platinum, rhenium, gold and silver, which have likewise been shaped by consolidating shaping processes. Such catalysts are described in DE-A 196 23 609.6, whose contents relating to the catalysts described there are wholly incorporated by reference into the present application.

As regards the consolidating shaping processes, the binders and the auxiliaries and the structure of the oxidation catalysts, the relevant contents of DE-A 196 23 611.8 are hereby incorporated by reference.

The oxidation catalyst described in DE-A 196 23 609.6 has a content of from 0.01 to 30% by weight, in particular from 0.05 to 15% by weight, especially from 0.1 to 8% by weight, in each case based on the amount of the titanium or vanadium zeolites, of the abovementioned noble metals. Particular preference is given to palladium. The noble metals can be applied to the catalyst in the form of suitable noble metal components, for example in the form of water-soluble salts, before, during or subsequent to the consolidating shaping step.

Furthermore, the following catalysts can be used according to the present invention:

A shaped body which comprises at least one porous oxidic material and is obtainable by a process comprising the following steps:

(I) admixing a mixture comprising a porous oxidic material or a mixture of two or more thereof with a mixture comprising at least an alcohol and water, and (II) kneading, shaping, drying and calcining the mixture obtained as described in step (I).

Details of this catalyst may be found in DE-A 197 23 751.7, whose contents are wholly incorporated by reference into the present application.

Furthermore, it is also possible, according to the present invention, to use solids which comprise silicon dioxide and are able to be prepared by a process comprising step (I) below:

(I) bringing at least one precursor of silicon dioxide into contact with at least one structure former in a liquid medium, wherein the structure former is a polyethylenimine or a mixture of two or more thereof.

Details regarding this solid may be found in DE-A 197 32 865.2, the contents of which are hereby wholly incorporated into the present application.

Further catalysts which can readily be used are shaped bodies which comprise an inert support and at least one silicate, preferably a crystalline silicate, applied thereto and are obtainable by application of a mixture comprising at least one silicate and at least one metalic acid ester or a hydrolysate thereof or a combination of metalic acid ester and hydrolysate thereof to the inert support, as described in DE-A 197 54 924.1, whose contents are wholly incorporated by reference into the present application.

Furthermore, it is possible, according to the present invention, to use shaped bodies which comprise at least one silicate and at least one metal oxide and are able to be prepared by a process comprising step (i) below:

(i) mixing the silicate or silicates with at least one metal oxide solution which has a low content of alkali metal ions and alkaline earth metal ions, as is described in DE-A 198 15 879.3.

The relevant contents of that application are likewise wholly incorporated by reference into the present application.

It is also possible, according to the present invention, to use titanium silicalites which have an RUT structure and can be prepared by a process comprising the steps (i) and (ii):

(i) preparation of a mixture of at least one $SiO_2$ source and at least one titanium source;

(ii) crystallization of the mixture from (i) in a pressure vessel with addition of at least one template compound to give a suspension, wherein the template compound used is an amine or ammonium salt which is suitable for stabilizing cages of the silicate structure $[4^4 5^4 6^2]$ and $[4^4 5^6 6^5 8^1]$.

Details of these catalysts may be found in DE-A 198 39 792.5.

It is also possible, according to the present invention, to use the silicon dioxides having mesopores and micropores described in: DE-A 198 47630.2, which preferably have one or more of the features (i) to (iii):

(i) the sum of the specific surface areas of the mesopores and micropores is at least 300 $m^2/g$;

(ii) the sum of the pore volumes of the mesopores and micropores is at least 0.2 m/g;

(iii) the maximum of the pore diameter distribution of the mesopores is at not less than 3 nm.

Further details regarding these catalysts may be found in the above-mentioned application, whose contents are wholly incorporated by reference into the present application.

Sheet silicates are silicates having a two-dimensionally linked silicate lattice and are described, for example, in R. M. Barrer "Zeolites and Clay Minerals as Sorbents and Molecular Sieves", Academic Press 1978, pages 407 if, in particular pages 413, 421 and 430. Particular mention may be made of attapulgite and sepiolite, pyrophyllite, talc, muscovite, paragonite, phlogopite, biotite, lepidolite, zinnwaldit, margarite, chloritoide, seyberite, vermiculites, smectites, e.g. montmorillonite, saponite, nontronite, beidellite, sauconite, hectorite, fluorhectorite, seladonite, glauconite, dioctahedral illite, trioctahedral illite, beidellite I and beidellite II.

On the other hand, clathrasils are three-dimensionally linked silicate structures whose network is nevertheless generally so narrow that no molecules having a kinetic diameter above 0.4 nm can be taken up, as is described, for example, in B. Marler, H. Gies "Zeolites", 15th edition, pages 5/7 (1995).

In a further preferred embodiment of the present process, the above-described silicate-containing catalysts are regenerated after complete or partial loss of activity and are preferably reused in the reaction according to the present invention. For the regeneration of the catalyst used according to the present invention, it is in principle possible to use all processes known from the prior art for regenerating silicate-containing catalysts, in particular zeolite catalysts. In general, the used catalyst is treated at from 20 to 700° C. in the presence or absence of oxygen or oxygen-donating substances so that the activity of the regenerated catalyst is higher than that of the used catalyst.

Specific mention may be made of the methods which have hitherto been described only for zeolite catalysts:

1. a process for regenerating an exhausted (zeolite) catalyst which comprises heating the exhausted catalyst at a temperature below 400° C. but above 150° C. in the presence of molecular oxygen for a period which is sufficient for increasing the activity of the exhausted catalyst, as is described in EP-A 0 743 094;

2. a process for regenerating an exhausted (zeolite) catalyst which comprises heating the exhausted catalyst at from 150° C. to 700° C. in the presence of a gas stream containing not more than 5% by volume of molecular oxygen for a period which is sufficient to improve the activity of the exhausted catalyst, as is described in EP-A 0 790 075;

3. a process for regenerating (zeolite) catalysts, in which the exhausted catalyst is heated at from 400 to 500° C. in the presence of an oxygen-containing gas or is washed with a solvent, preferably at a temperature which is 5-150° C. higher than the temperature used during the reaction, as is described in JP 3 11 45 36;

4. a process for regenerating an exhausted (zeolite) catalyst by calcining it at 550° C. in air or by washing with solvents, thus restoring the activity of the catalyst, as is described in "Proc. 7th Intern. Zeolite Conf. 1986 (Tokyo)";

5. a process for regenerating a (zeolite) catalyst comprising steps (I) and (II) below:

(I) heating an at least partially deactivated catalyst to a temperature in the range from 250° C. to 600° C. in an atmosphere containing less than 2% by volume of oxygen, and (II) treating the catalyst at a temperature in the range from 250 to 800° C., preferably from 350 to 600° C., with a gas stream having a content of an oxygen-donating substance or of oxygen or of a mixture of two or more thereof in the range from 0.1 to 4% by volume, and optionally the further steps (II) and (IV), (III) treating the catalyst at a temperature in the range from 250 to 800° C., preferably from 350 to 606° C., with a gas stream having a content of an oxygen-donating substance or of oxygen or of a mixture of two or more thereof in the range from >4 to 100% by volume, (IV) cooling the regenerated catalyst obtained in step (111) in an inert gas stream containing up to 20% by volume of the vapor of a liquid selected from the group consisting of water, alcohols, aldehydes, ketones, ethers, acids, esters, nitrites, hydrocarbons and mixtures of two or more thereof.

Details of this process may be found in DE-A 197 23 949.8.

As regards the reaction conditions in the process of the present invention, there are no particular restrictions. The reaction can be carried out at subatmospheric, atmospheric or superatmospheric pressures, depending on the reaction temperature used. This is generally in the range from about 25 to about 150° C., preferably from about 50 to about 120° C. and in particular from about 70 to about. 100° C.

As solvent, it is possible to use either organic solvents or water or mixtures thereof. Preference is given to carrying out the reaction in aqueous solution or suspension.

The reaction time is in the range from one minute to a plurality of hours. There are no restrictions in respect of the molar ratio of oxidant to PMIDE; preference is given to using at least 0.5 mol, more preferably at least 1 mol, of oxidant per mol of PMIDE.

As already mentioned, the reaction mixture can be brought into contact with the catalyst either in suspension or in a fixed bed. The reaction can be carried out batchwise or continuously.

To avoid safety risks, the oxygen content during the reaction is generally set so that the composition is reliably outside the explosive limits. This is achieved, for example, by mixing in suitable inert gases such as nitrogen.

The present invention is illustrated by the examples below:

EXAMPLES

Example 1

In a 250 ml three-necked flask fitted with stirrer, dropping funnel and reflux condenser, 20 g of catalyst (Cr/zeolite having a BEA structure and a chromium content of 2.8% by weight) in 100 ml of deionized water were combined with 34 g of PMIDE and heated to 85° C. while stirring. After this temperature had been reached, 70 ml of a 30% strength by weight $H_2O_2$ solution were added and the solution was allowed to react for 1 hour. After cooling, the catalyst was separated off and the clear reaction solution was analyzed. The glyphosate content was determined as 3.2% by weight by means of HPLC using UV detection; this corresponds to a yield of 18 mol % based on PMIDE used.

Example 2

Example 1 was repeated using 20 g of montmorillonite (bulk density: 670 g/l; specific surface area: 230 m²/g) as catalyst. The glyphosate content of the resulting reaction mixture was 6.60% by weight, corresponding to a yield of 44% based on PMIDE used.

We claim:

1. A process for preparing N-phosphonomethylglycine or a salt thereof by bringing phosphonomethyliminodiacetic acid or a salt thereof into contact with at least one oxygen-containing oxidant in the presence of a heterogeneous catalyst comprising at least one silicate, with the proviso that the process is not an oxidative cleavage of N-phosphonomethyliminodiacetic acid with simultaneous oxidation of formaldehyde formed as by-product in the presence of a catalyst system which comprises activated carbon together with a microporous acid-resistant aluminosilicate having a ratio of Si to Al of at least 2 as support and a noble metal as active component.

2. A process as claimed in claim 1, wherein the oxygen-containing oxidant or oxidants is/are selected from the group consisting of hydroperoxides, gases containing molecular oxygen, oxygen-donating compounds, nitrogen oxides and mixtures of two or more thereof.

3. A process as claimed in claim 1 wherein the silicate or silicates is/are selected from the group consisting of zeolites, sheet silicates, naturally occurring or synthetically produced clay minerals, clathrasils and mixtures of two or more thereof.

4. A process as claimed in claim 2, wherein the silicate or silicates is/are selected from the group consisting of zeolites, sheet silicates, naturally occurring or synthetically produced clay minerals, clathrasils and mixtures of two or more thereof.

5. A process as claimed in claim 1, wherein the crystalline dilicate or silicates is/are selected from the group consisting of zeolite structure-types having framework type codes ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, COO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG and ZON, and mixtures of two or more thereof.

6. A process as claimed in claim 2, wherein the crystalline dilicate or silicates is/are selected from the group consisting of zeolite-structure types having framework type codes ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG and ZON, and mixtures of two or more thereof.

7. A process as claimed in claim 3, wherein the crystalline dilicate or silicates is/are selected from the group consisting of zeolite-structure types having framework type codes ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG and ZON, and mixtures of two or more thereof.

8. A process as claimed in claim 4, wherein the crystalline dilicate or silicates is/are selected from the group consisting of zeolite-structure types having framework type codes ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG and ZON, and mixtures of two or more thereof.

9. A process as claimed in claim 1, wherein the at least one heterogeneous catalyst further comprises at least one element selected from among the elements of groups Ia, IIa, IIIa, IVa, Va, VIIa, VIIa, VIIIa, Ib, IIb, IIIb, IVb, Vb, VIIb, VIIb of the Periodic Table.

10. A process as claimed in claim 2, wherein the at least one heterogeneous catalyst further comprises at least one element selected from among the elements of groups Ia, Ia, IIIa, IVa, Va, VIIa, VIIa, VIIIa, Ib, IIb, IIIb, IVb, Vb, VIb, VIIb of the Periodic Table.

11. A process as claimed in claim 3, wherein the at least one heterogeneous catalyst further comprises at least one element selected from among the elements of groups Ia, IIa, IIIa, IVa, Va, VIIa, VIIa, VIIIa, Ib, IIb, IIIb, IVb, Vb, VIIb, VIIb of the Periodic Table.

12. A process as claimed in claim 4, wherein the at least one heterogeneous catalyst further comprises at least one element selected from among the elements of groups Ia, IIa, IIIa, IVa, Va, VIIa, VIIa, VIIIa, Ib, IIb, IIIb, IVb, Vb, VIIb, VIIb of the Periodic Table.

13. A process as claimed in claim 5, wherein the at least one heterogeneous catalyst further comprises at least one element selected from among the elements of groups Ia, IIa, IIIa, IVa, Va, VIIa, VIIa, VIIIa, Ib, IIb, IIIb, IVb, Vb, VIIb, VIIb of the Periodic Table.

14. A process as claimed in claim 1, wherein the heterogeneous catalyst is regenerated after complete or partial loss of activity and the regenerated heterogenous catalyst is reused for preparing N-phosphonomethylglycine or a salt thereof from phosphonomethyliminodiacetic acid or a salt thereof.

15. A process as claimed in claim 2, wherein the heterogeneous catalyst is regenerated after complete or partial loss of activity and the regenerated heterogeneous catalyst is reused for preparing N-phosphonomethylglycine or a salt thereof from phosphonomethyliminodiacetic acid or a salt thereof.

16. A process as claimed in claim 3, wherein the heterogeneous catalyst is regenerated after complete or partial loss of activity and the regenerated heterogeneous catalyst is reused for preparing N-phosphonomethylglycine or a salt thereof from phosphonomethyliminodiacetic acid or a salt thereof.

17. A process as claimed in claim 4, wherein the heterogeneous catalyst is regenerated after complete or partial loss of activity and the regenerated heterogeneous catalyst is reused for preparing N-phosphonomethylglycine or a salt thereof from phosphonomethyliminodiacetic acid or a salt thereof.

18. A process as claimed in claim 5, wherein the heterogeneous catalyst is regenerated after complete or partial loss of activity and the regenerated heterogeneous catalyst is reused for preparing N-phosphonomethylglycine or a salt thereof from phosphonomethyliminodiacetic acid or a salt thereof.

19. A process for preparing N-phosphonomethylglycine or a salt thereof by bringing phosphonomethyliminodiacetic acid or a salt thereof into contact with at least one oxygen-containing oxidant selected from a group consisting of hydroperoxides, gases containing molecular oxygen, oxygen-donating compounds, nitrogen oxides and mixtures of two or more thereof; in the presence of a heterogeneous catalyst, comprising at least one silicate selected from the group consisting of zeolites, sheet silicates, naturally occurring or synthetically produced clay minerals, clathrasils and mixtures of two or more thereof, with the proviso that the process is not an oxidative cleavage of N-phosphonomethyliminodiacetic acid with simultaneous oxidation of formaldehyde formed as by-product in the presence of a catalyst system which comprises activated carbon together with a microporous acid-resistant aluminosilicate having a ratio of Si to Al of at least 2 as support and a noble metal as active component.

20. A process as claimed in claim 19, wherein the zeolites are selected from the group consisting of zeolites of the structure types having framework type codes ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG and ZON, and mixtures of two or more thereof.

21. A process as claimed in claim 19, wherein the at least one heterogeneous catalyst further comprises at least one element selected from among the elements of groups Ia, IIa, IIIa, IVa, Va, VIIa, VIIa, VIIIa, Ib, IIb, IIIb, IVb, Vb, Vab, VIIb of the Periodic Table.

22. A process as claimed in claim 19, wherein the heterogeneous catalyst is regenerated after complete or partial loss of activity and the regenerated heterogeneous catalyst is reused for preparing N-phosphonomethylglycine or a salt thereof from phosphonomethyliminodiacetic acid or a salt thereof.

* * * * *

UNITED STATES PATENT AND TRADEMARK OFFICE
CERTIFICATE OF CORRECTION

PATENT NO.    : 6,867,326 B1
DATED         : March 15, 2005
INVENTOR(S)   : Müller et al.

It is certified that error appears in the above-identified patent and that said Letters Patent is hereby corrected as shown below:

<u>Column 8,</u>
Line 38, delete:
"COO, HEU, IFR, ISV, ITE, JBW, KFI, LAU, LEV, LIO," and substitute
-- GOO, HEU, IFR, ISV, ITE, JBW, KFI, LAU, LEV, LIO, --.

<u>Column 9,</u>
Line 25, delete:
"MWW, NAT, NES, NON, OFF, OSI PAR, PAU, PHI, RHO," and substitute
-- MWW, NAT, NES, NON, OFF, OSI, PAR, PAU, PHI, RHO, --.
Line 33, delete:
"IIIa IVa,Va, VIIa, VIIa, VIIIa, Ib, IIb, IIIb, IVb, Vb, VIIb," and substitute
-- IIIa, IVa, Va, VIa, VIIa, VIIIa, Ib, IIb, IIIb, IVb, Vb, VIb, --.
Line 37, delete:
"element selected from among the elements of groups Ia, Ia," and sustitute
-- element selected from among the elements of groups Ia, IIa, --.
Line 38, delete:
"IIIa, IVa, Va, VIIa, VIIa, VIIIa, Ib, IIb, IIIb, IVb, Vb, VIIb," and substitute
-- IIIa, IVa, Va, VIa, VIIa, VIIIa, Ib, IIb, IIIb, IVb, Vb, VIb, --.
Line 43, delete:
"IIIa, IVa, Va, VIIa, VIIa, VIIIa, Ib, IIb, IIIb, IVb, Vb, VIIb," substitute
-- IIIa, IVa, Va, VIa VIIa, VIIIa, Ib, IIb, IIIb, IVb, Vb, VIb, --.
Line 48, delete:
"IIIa, IVa, Va, VIIa, VIIa, VIIIa, Ib, IIb, IIIb, IVb, Vb, VIIb," and substitute
-- IIIa, IVa, Va, VIa, VIIa, VIIIa, Ib, IIb, IIIb, IVb, Vb, VIb, --.
Line 53, delete:
"IIIa, IVa, Va, VIIa, VIIa, VIIIa, Ib, IIb, IIIb, IVb, Vb, VIIb," and substitute
-- IIIa, IVa, Va, VIa, VIIa, VIIIa, Ib, IIb, IIIb, IVb, Vb, VIb, --.

UNITED STATES PATENT AND TRADEMARK OFFICE
CERTIFICATE OF CORRECTION

PATENT NO. : 6,867,326 B1
DATED : March 15, 2005
INVENTOR(S) : Müller et al.

It is certified that error appears in the above-identified patent and that said Letters Patent is hereby corrected as shown below:

<u>Column 10,</u>
Line 57, delete:
"IIIa, IVa, Va, VIIa, VIIa, VIIIa, Ib, IIb, IIIb, IVb, Vb, Vab," and substiute
-- IIIa, IVa, Va, VIa, VIIa, VIIIa, Ib, IIb, IIIb, IVb, Vb, VIb, --.

Signed and Sealed this

Thirtieth Day of May, 2006

JON W. DUDAS
*Director of the United States Patent and Trademark Office*